United States Patent
Edd et al.

(10) Patent No.: US 9,677,064 B2
(45) Date of Patent: Jun. 13, 2017

(54) MICROFLUIDIC DROPLET ENCAPSULATION

(71) Applicant: The General Hospital Corporation, Boston, MA (US)

(72) Inventors: Jon F Edd, Arlington, MA (US); Memhet Toner, Charlestown, MA (US); Dino DiCarlo, Los Angeles, CA (US); Daniel Irimia, Charlestown, MA (US)

(73) Assignee: The General Hospital Corporation, Boston, MA (US)

(*) Notice: Subject to any disclaimer, the term of this patent is extended or adjusted under 35 U.S.C. 154(b) by 72 days.

(21) Appl. No.: 14/754,420

(22) Filed: Jun. 29, 2015

(65) Prior Publication Data
US 2015/0361414 A1  Dec. 17, 2015

Related U.S. Application Data

(62) Division of application No. 12/472,346, filed on May 26, 2009, now Pat. No. 9,068,181.

(60) Provisional application No. 61/055,653, filed on May 23, 2008.

(51) Int. Cl.
*C12N 11/04* (2006.01)

(52) U.S. Cl.
CPC .................. *C12N 11/04* (2013.01)

(58) Field of Classification Search
CPC .... C12N 11/04; B82Y 30/00; B01L 3/502746
USPC ...... 435/287.2, 288.5, 306.1, 174, 182, 178, 435/382, 395, 283.1, 440; 424/93.7, 450, 424/423, 93.1, 400, 408, 451, 455; 428/402–402.24, 403, 404, 407, 321.1, 428/474.4; 427/331, 389.9, 212, 427/213–213.36, 483, 256, 213.3, 213.34, 427/214
See application file for complete search history.

(56) References Cited

U.S. PATENT DOCUMENTS

| | | | |
|---|---|---|---|
| 5,968,820 A | 10/1999 | Zborowski et al. | |
| 6,540,895 B1 | 4/2003 | Spence et al. | |
| 6,767,706 B2 | 7/2004 | Quake et al. | |
| 8,658,418 B2 * | 2/2014 | Daridon | G02B 21/32 435/287.2 |
| 9,068,181 B2 | 6/2015 | Edd et al. | |
| 2002/0058332 A1 * | 5/2002 | Quake | B01L 3/502784 435/288.5 |
| 2006/0051329 A1 * | 3/2006 | Lee | B01F 3/0807 424/93.7 |
| 2009/0014360 A1 | 1/2009 | Toner et al. | |
| 2010/0021984 A1 | 1/2010 | Edd et al. | |
| 2010/0022680 A1 * | 1/2010 | Karnik | B82Y 30/00 523/105 |

FOREIGN PATENT DOCUMENTS

WO  2007044690  4/2007

OTHER PUBLICATIONS

Utada et al., 'Dripping to Jetting Transitions in Coflowing Liquid Streams', Phys. Rev. Lett. 99, 094502 (2007).
Edd et al., 'Controlled encapsulation of single-cells into monodisperse picolitre drops', Lab on a Chip, 2008, 8, 1262-1264.
Edd et al., 'Controlled encapsulation of single cells into monodisperse picolitre drops', Supplementary Materials (ESI) for Lab on a Chip, pp. 1-8, 2008.
Anna et al., "Formation of dispersions using "flow focusing" in microchannels", Applied Phys. Lett., 82, 364-366 (2003).
Cooper et al., 'Chips & tips: Preventing suspension settling during injection', Lab on a Chip, Aug. 21, 2007.

* cited by examiner

*Primary Examiner* — Douglas MC Ginty
(74) *Attorney, Agent, or Firm* — Fish & Richardson P.C.

(57) ABSTRACT

Microfluidic devices and methods for the encapsulation of particles within liquid droplets are disclosed. The new methods and devices form 1-100 picoliter-size monodisperse droplets containing the particles, such as single cells, encapsulated in individual liquid droplets. The particles can be encapsulated in droplets of a fluid by passing a fluid containing the particles through a high aspect-ratio microchannel to order the particles in the fluid, followed by forming the fluid into droplets. The resulting fraction of the liquid droplets with a single particle (e.g., a cell) is higher than the corresponding fraction of single-particle liquid droplets predicted by Poisson statistics.

20 Claims, 14 Drawing Sheets a

A	B	C

US 9,677,064 B2

MICROFLUIDIC DROPLET ENCAPSULATION

RELATED APPLICATIONS

This application is a divisional of U.S. application Ser. No. 12/472,346, filed on May 26, 2009, now U.S. Pat No. 9,068,181, which claims the benefit of U.S. provisional patent application Ser. No. 61/055,653, filed on May 23, 2008. The subject matter of this U.S. provisional patent application is incorporated herein by reference in its entirety.

STATEMENT OF FEDERALLY SPONSORED RESEARCH

This application was made with Government support under Grant Nos. DMR0213805, DMR0602684, and DEI0649865 awarded by the National Science Foundation and Grant No. EB002503 awarded by the Public Health Services/National Institutes of Health. The Government has certain rights in this invention.

TECHNICAL FIELD

This disclosure relates to the encapsulation of analyte material, such as cells, in liquid droplets.

BACKGROUND

Microfluidic devices and methods promise breakthrough applications in biotechnology such as directed evolution, tissue printing, and bead-based PCR in emulsions, while facilitating many quantitative studies of biology at a single-cell level. For example, in some microfluidic methods, individual cells can be made to reside within separate picoliter-volume liquid drop, chemically isolated from other droplets. This can permit cell-secreted molecules to rapidly achieve detectable concentrations in a confined fluid droplet surrounding the encapsulated cell. Similarly, uptake of trace chemicals specific to individual cells can be probed due to their depletion within the confined extracellular fluid. Moreover, highly monodisperse droplets of water in an inert and immiscible carrier fluid can be formed at rates of several kHz using microfluidic techniques. These droplets can be combined in pairs, split in two, and selected based on the contents of individual droplets. However, variability in the number of cells or other particles per drop of fluid due to stochastic cell loading is a major barrier to an effective use of these techniques.

Existing processes for loading individual cells into droplets are typically random processes with the distribution of the number of cells in each droplet being dictated by Poisson statistics. Accordingly, the probability of a drop containing k cells is $\lambda^k \exp(-\lambda)/(k!)$, where k is the average number of cells per drop. The ratio of droplets containing one cell to those containing two is $2/\lambda$. This means that to minimize the number of droplets that contain more than a single cell requires very low average loading densities. As a result, most droplets actually contain no cells whatsoever. This constraint significantly reduces the number of usable droplets. For example, only 15.6% of all droplets will contain one cell if no more than one in ten of the occupied droplets can be allowed to hold two or more cells. There is a need for microfluidic devices and methods for forming a higher proportion of liquid droplets containing a single cell.

SUMMARY

Microfluidic devices and methods disclosed herein provide encapsulation of particles within liquid droplets, including formation of picoliter-size monodisperse droplets containing the particles. By ordering the particles in a fluid stream within a microfluidic channel before droplet formation, droplets containing a single particle can be formed. The particles can be living cells or other material derived from a biological fluid sample, such as blood, or synthetic materials, such as polymeric beads. For example, fluid droplets containing a single cell can be repeatedly generated in an aqueous fluid (e.g., a saline solution). The invention is based, in part, on the discovery that passing a particle (e.g., solid analyte particles, or cells) rapidly through a high aspect-ratio microchannel and into a droplet generator results in the formation of a desirable fraction of liquid droplets with a single particle per droplet. In general, the microchannel dimensions and fluid flow rate can be selected using criteria described herein to provide a fluid stream of ordered particles substantially evenly spaced along the length of the microchannel before entering the droplet generator. In addition, particles, e.g., cells, tend to enter the droplet generator with the frequency of droplet formation. In the resulting droplets, the fraction of single-particle liquid droplets is higher than the corresponding fraction of single-particle liquid droplets predicted by Poisson statistics.

In one aspect, the invention features methods of encapsulating particles in liquid droplets. The methods include passing a particle (e.g., cells) through a channel in a fluid medium and forming the fluid medium into a plurality of droplets. In one example, the largest particle has a maximum cross-sectional dimension that is at least about 10% (e.g., 10% to about 40%, including 10-40, 20-30, 25, 30, or 35%) of the smallest cross-sectional dimension of the channel through which the fluid passes. The plurality of particles in the fluid medium through a channel can have a minimum cross-sectional dimension D, wherein the largest particles in the plurality has a maximum cross-sectional dimension that is at least about 0.1D (e.g., about 0.1 D to 0.4D). The fluid medium can be formed into a plurality of picoliter droplets containing k particles outside the channel, wherein the proportion of the droplets containing k particles is greater than $\lambda^k \exp(-\lambda)/(k!)$ (i.e., the proportion given by random, Poisson statistics), when $\lambda$ is the average number of particles per droplet. For example, the proportion of droplets containing one particle is greater than $\lambda^k \exp(-\lambda)$, including a proportion of droplets containing one particle of at least about $0.9\lambda$. The proportion of droplets containing only one particle can be at least about 90% of the total number of droplets. The particle in the fluid medium leaving the channel to form the plurality of droplets preferably includes particles having a substantially uniform spacing with respect to adjacent particles in the direction of the fluid medium flow In certain of these methods, forming the fluid medium into a plurality of droplets can include contacting the fluid medium with a second medium (e.g., an oil) immiscible in the first medium (e.g., an aqueous solution) to form the droplets in the second medium. For example, the fluid medium can be passed through a nozzle or other droplet generating device to form the plurality of droplets.

In another aspect, the invention features systems for encapsulating particles in a fluid medium. The systems can include a microfluidic channel having a minimum cross-sectional dimension D adapted to receive a fluid medium containing a plurality of particles having a maximum individual cross-sectional dimension of at least about 0.1D, and a droplet generator in fluid communication with the microfluidic channel. The microfluidic channel is configured to passively order the particles within the fluid medium while passing through the microfluidic channel. For example, the microfluidic channel can have a dimension D that is less than 1 mm, including 10-100 micrometers, and can be straight or curved. The droplet generator can include a nozzle at an outlet of the microfluidic channel. The droplet generator can also include a vessel containing a second fluid medium that is immiscible in the fluid medium exiting from the microfluidic channel. The droplet generator can produce droplets of the fluid medium in the second fluid medium outside of the microfluidic channel.

The methods and devices described herein are useful, in particular, for loading particles into droplets for applications that demand minimal numbers of empty droplets in addition to a high ratio of single-cell droplets to multiples. For example, the methods and devices can be used in the creation of tissue engineered constructs by "printing" cells onto a substrate as a spray of picoliter-size aqueous droplets in air will receive a significant boost in resolution from this ability to control cell loading, allowing the narrowest possible lines to become the width of a single-cell. Such ordered encapsulation becomes even more important for applications where streams of droplets, each with single-particles of two varieties, are combined to create larger droplets carrying exactly one particle of each kind; the number of suitable droplets for the above conditions would rise from 0.15% without ordering to about 80%, about 500 times higher.

Unless otherwise defined, all technical and scientific terms used herein have the same meaning as commonly understood by one of ordinary skills in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

As used herein, unless otherwise indicated, the term "particle" refers to a small discrete mass of solid or liquid matter, such as a cell or a solid particle that can be discretely transported in a fluid stream.

As used herein, unless otherwise indicated, the term "fluid" refers to a gas or liquid, such a liquid biological sample (e.g., whole blood).

DESCRIPTION OF THE DRAWINGS

In FIGS. 7A-7B, the droplets enclosed by a white circle have one particle per droplet; the droplets enclosed by a square circle have two particles per droplet and the droplets that are not surrounded by a white circle or square do not contain a particle.

DETAILED DESCRIPTION

Figure 1:
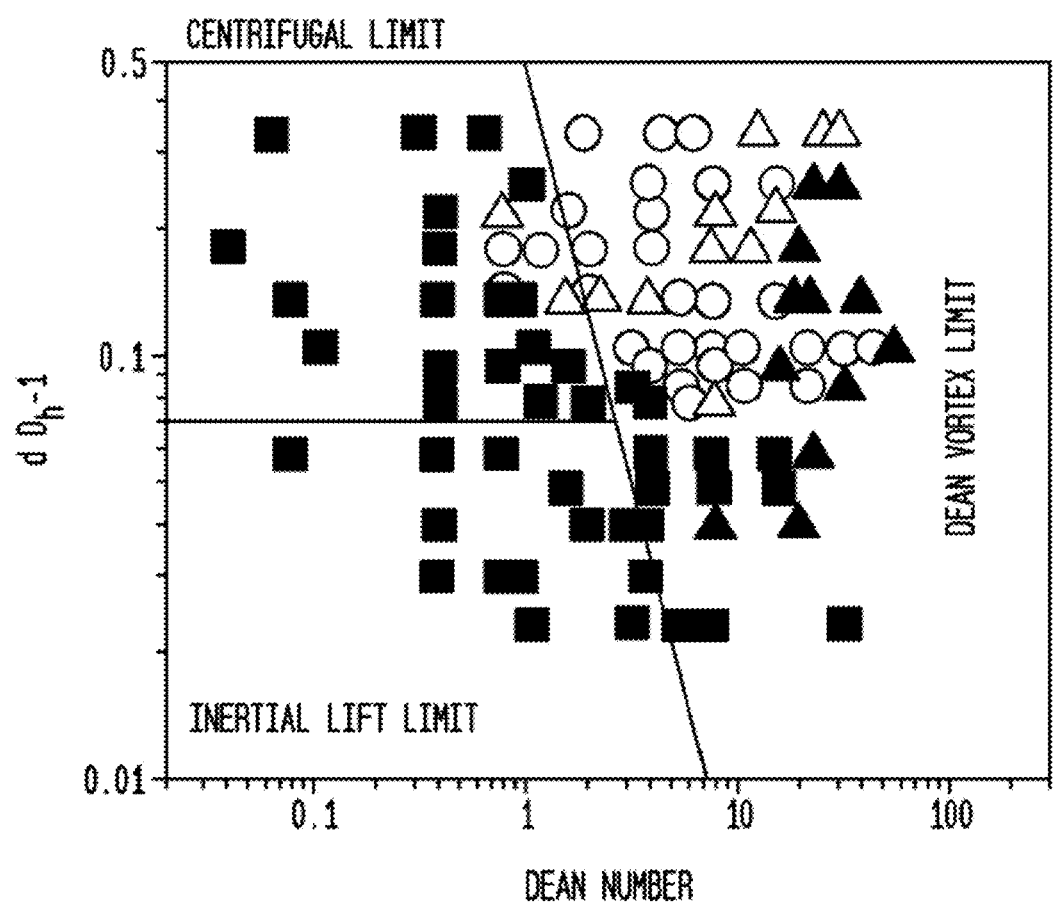
FIG. 1 is a graph showing parameters useful in predicting when particle ordering can occur within a fluid passing through a microfluidic channel.

Particles (e.g., cells or particles), in a fluid stream can be encapsulated in individual droplets by first forming an ordered stream of particles in the fluid stream within a microchannel and then forming the fluid stream containing the ordered stream of particles into droplets each containing, on average, a single particle. For example, a fluid stream entering a droplet forming nozzle can contain two evenly-spaced streams of particles (e.g., cells) whose longitudinal order is shifted by half the particle-particle spacing. Ordering of the particle within the fluid stream can occur when a high density suspension of particles (e.g., cells or particles) is forced to travel rapidly through a high aspect-ratio microchannel, where particle diameter is a large fraction (e.g., 10-40%) of the channel's narrowest cross-sectional dimension (i.e., a microfluidic channel having at least one cross-sectional dimension that is about 2.5 to about 10 times the width of the largest dimension of the particles). This phenomenon provides a method to controllably load single-cells into droplets, overcoming the intrinsic limitations set by Poisson statistics and ensuring that a high percentage (e.g., 90% or more) of the droplets contains exactly one cell.

Various microchannel configurations can be used to produce the ordered particle fluid stream that can be used for droplet formation. Particles order laterally within the x-y plane (or cross-sectional plane) of the channel and can also order longitudinally along the direction of flow. An additional dimension of rotational ordering can occur for asymmetrically shaped particles. The speed and number (or concentration) of the particles can be selected to provide a higher proportion of droplets containing a single particle than would be predicted by a random statistical model absent the ordering of the particles within the fluid before droplet formation.

Unless otherwise indicated, as used herein, a "sample" refers to a fluid (e.g., gas or liquid) capable of flowing through a channel. Thus, a sample can include a fluid suspension of biologically-derived particles (such as cells). The sample can comprise a material in the form of a fluid suspension that can be driven through microfluidic channels can be used in the systems and methods described herein. For example, a sample can be obtained from an animal, water source, food, soil, or air. If a solid sample is obtained, such as a tissue sample or soil sample, the solid sample can be liquefied or solubilized prior to subsequent introduction into the system. If a gas sample is obtained, it may be liquefied or solubilized as well. The sample may also include a liquid or gas as the particle. For example, the sample may comprise bubbles of oil or other kinds of liquids or gases as the particles suspended in an aqueous solution. A sample can generally include suspensions, liquids, and/or fluids having at least one type of particle, cellular, droplet, or otherwise, disposed therein. Further, focusing can produce a flux of particles enriched in a first particle based on size. Exemplary particles can include, but are not limited to, cells, alive or fixed, such as adult red blood cells, fetal red blood cells, trophoblasts, fetal fibroblasts, white blood cells, epithelial cells, tumor cells, cancer cells, hematopoeitic stem cells, bacterial cells, mammalian cells, plant cells, neutrophils, T lymphocytes, B lymphocytes, monocytes, eosinophils, natural killer cells, basophils, dendritic cells, circulating endothelial cells, antigen specific T-cells, and fungal cells.

Samples can be diluted or concentrated to attain a predetermined ratio before and/or during introduction of the sample into the system. In general, the particle to volume ratio can be less than about 50%. In other embodiments, particle to volume ratios can be less than about 40%, 30%, 20%, 10%, 8%, or 6%. More particularly, in some embodiments, particle to volume ratios can be in a range of about 0.001% to about 5%, e.g., in a range of about 0.01% to about 4%. The ratio can also be in the range of about 0.1% to about 3%, e.g., in the range of about 0.5% to about 2%. In general, a maximum particle to volume ratio for a specified particle size and channel geometry can be determined using the formula:

$$\text{Max Volume Fraction} = \frac{2N\pi a^2}{3hw}$$

where N is the number of focusing positions in a channel, a is the focused particle diameter, h is the channel height, and w is the channel width. The focusing position refers to a volume where the equilibrium positions of flowing particles converge within a channel. A fluid sample can be diluted or concentrated in batches before introduction into the channel such that the sample ultimately introduced into the system has the required ratio before being introduced to the channel.

Particles suspended within a sample can have any size that allows them to be ordered and focused within the microfluidic channels described herein. For example, particles can have a hydrodynamic size that is in the range of about 40 microns to about 0.01 microns. For example, particles can have a hydrodynamic size that is in the range of about 20 microns to about 0.1 microns; particles can also have a hydrodynamic size that is in the range of about 10 microns to about 1 micron.

Various microfluidic systems and channel geometries can result in longitudinally ordered particles in the direction of flow. Microchannel configurations for ordering a plurality of particles in a fluid stream passing through the microchannel can be designed based on certain parameters relating to the particle size and the microchannel dimensions, including the channel Reynolds number (Rc), the particle Reynolds number (Rp), the Reynolds number based on mean channel velocity (Re), the particle hydraulic diameter (Dh) and the Dean Number (De).

The channel Reynolds number (Rc) describes the unperturbed channel flow: Rc=(UmDh)/v. The particle Reynolds number (Rp) includes parameters describing both the particle and the channel through which it is translating: $R_p = R_c (a^2/D_h^2) = (U_m a^2)/vD$. Both dimensionless groups depend on the maximum channel velocity, $U_m$, the kinematic viscosity of the fluid, and v=μ/ρ (μ and ρ being the dynamic viscosity and density of the fluid, respectively), and $D_h$, the hydraulic diameter, defined as 2wh/(w+h) (w and h being the width and height of the channel). The particle Reynolds number has an additional dependence on the particle diameter, a.

The definition of Reynolds number based on the mean channel velocity can be related to Rc by $R_e 2/3 R_c$. Channels with curvature create additional drag forces on particles. When introducing curvature into rectangular channels, secondary flows develop perpendicular to the streamwise direction due to the nonuniform inertia of the fluid. Two dimensionless numbers can be written to characterize this flow, the Dean number (De) based on the maximum velocity in the channel, and the curvature ratio (δ). The Dean number, De=Rc $(D_h/2r)^{1/2}$ and the curvature ratio, $\delta = D_h/2r$, where r is the average radius of curvature of the channel.

Using these parameters, microchannel dimensions and configurations providing focusing of particles within a fluid stream. Various combinations of these parameters will result in localization of a flux of particles in a channel with a given channel geometry. Preferably, particles are passed through a microfluidic channel with a Rp of about 1 or greater. In general, the Reynolds number of the flowing sample can be about 1 to about 250, the Dean number of the flowing sample around a curved microchannel can be less than about 30, preferably about 20 or less, and/or the ratio of particle diameter to hydraulic diameter can be less than about 0.5. Channel cross-sections can include, but are not limited to, square, rectangular, circular, triangular, diamond, and hemispherical. Particles of a predetermined size can be focused in each of these exemplary cross-sections, and the equilibrium positions will be dependent on the geometry of the channel.

FIG. 1 is a graph of focusing results for particles as a function of two parameters, hydraulic diameter ($D_h$) versus Dean number. The data in FIG. 1 was obtained by measuring the particle focusing of range of particle diameters (2-17 μm) and channel sizes ($D_h$=10-87 μm) over a range of Rc=0.075-225 for curving asymmetric channels. The focusing results were plotted as a function of De and the ratio a/$D_h$, as shown in FIG. 1. In FIG. 1, no particle focusing corresponds to filled squares, focusing to two streams corresponds to open triangles, focusing to a single stream is represented by open circles, and more complex behavior is shown as filled triangles. Data for this graph was collected using various size particles (2-17 μm) as well as four different channel geometries, as described in co-pending patent application Ser. No. 12/103,885 (filed Apr. 16, 2008), which is incorporated herein by reference in its entirety.

The results shown in FIG. 1 apply universally for any diameter ratio and Dean number falling within a specific region independent of the specific geometry. The data plotted in FIG. 1 appear similar to a phase diagram and are useful for determining the suitable microfluidic channels. A vertical movement on the diagram corresponds to changing particle size if channel geometries are held constant. To effect a focusing of particles in a fluid stream, one can choose a region in the phase diagram (i.e., a specific geometry) where a small change in particle size leads to a change from a focused to an unfocused stream. Thus, one particle size is focused to a particular streamline and can be collected as an enriched fraction, whereas the other, smaller, particles are unfocused. Numerous systems and methods for producing a focused stream of particles in a fluid stream are described in co-pending patent application Ser. No. 12/103,885 (filed Apr. 16, 2008), and are incorporated herein by reference in their entirety.

Particle size (at least over the range of cell diameters) had a minor role in cross-stream ordering behavior. Inertial lift forces that lead to focusing of particles in the lateral dimension of the channel are known to scale strongly with particle size, such that for the tested system cells and particles with diameters below ~4 µm were seen to have less robust ordering. For larger particles, the limitation is based on the minimum channel dimension ~27 µm. Generation of ordered streams for particles above and below these limits (e.g. bacteria and plant cells) is expected to be possible by changing the channel dimensions appropriately. Limitations could arise for scaling to smaller dimensions as the pressure drop per unit channel length in the absence of particles is approximately equal to $$32\mu \bar{V}\left(\frac{w+h}{2wh}\right)^2,$$

where µ is dynamic viscosity, V is the average fluid velocity and w and h are the channel width and height respectively.

Referring now to FIGS. 2A-2D, cell ordering in a rectangular geometry channel for straight is described. The separation, ordering, and focusing of particles can occur within these exemplary straight channels. In general, at low flow rates, particles flowing within these exemplary channels distribute uniformly along the length of a channel having (1) a cross-sectional aspect ratio (i.e., ratio of length to width or vice versa) of about 1.5 to 8.0 (preferably about 1.5 to 4.0), and (2) a minimum cross-sectional dimension that is up to about 10 times (e.g., 2.5-10 times) the maximum cross-sectional dimension of a particle passing through the channel in a fluid. In the illustrated embodiment, particles 9 µm in diameter suspended in water were observed in 50 µm-wide square channels, providing a particle diameter to channel diameter of 0.18. An inlet region is shown where the particles are initially uniformly distributed within the fluid but start to focus shortly thereafter to the four channel faces. The degree of focusing increases with Rp at a given distance along the channel and also increases with the distance traveled along the channel. Preferably the particle Reynolds number is about 1 or greater. For Rp=2.9 (Rc=90), complete focusing is observed after a distance of about 1 cm.

Figure 2A:
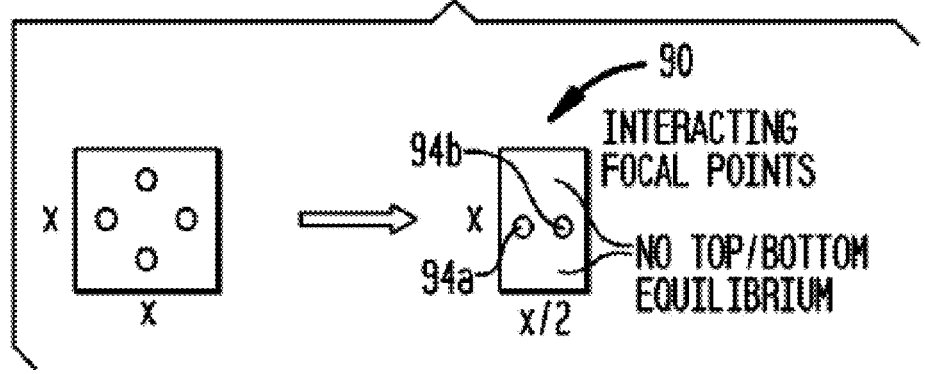
FIGS. 2A-2D are a series of schematic diagrams showing the ordering of particles flowing through a straight microfluidic channel.

The cross-section of a straight channel 90 can be adjusted to produce specific and/or optimized focusing results. In particular, the aspect ratio of the channel 90 cross-section can be changed from about 1 to 1 to about 2 to 1 as shown in FIG. 2A. In addition, the particle diameter to channel diameter ratio is preferably greater than 0.3. When the aspect ratio and the particle diameter to channel diameter are adjusted in this way, less deviation in position is observed during particle focusing in the channel 90. In addition, particles (e.g., cells) in the two ordering sites 94 a, 94 b are observed to interact and order across the channel 90. Ordering can occur for low to high particle concentrations, where only the particle-particle distance is affected by concentration. Importantly, particles can become evenly spaced in the direction of flow even to high particle concentration (e.g., $50 \times 10^6$/ml).

Figure 2B:
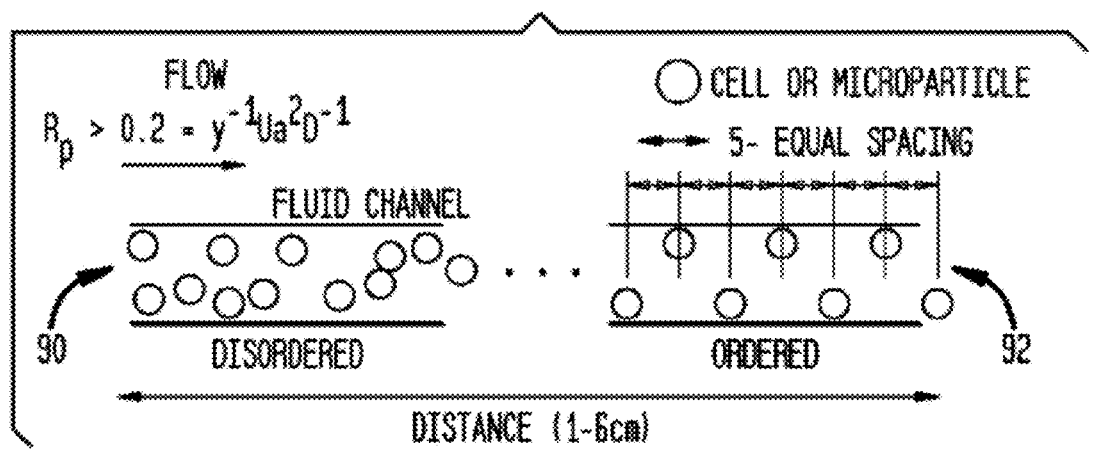
Figure 2C:
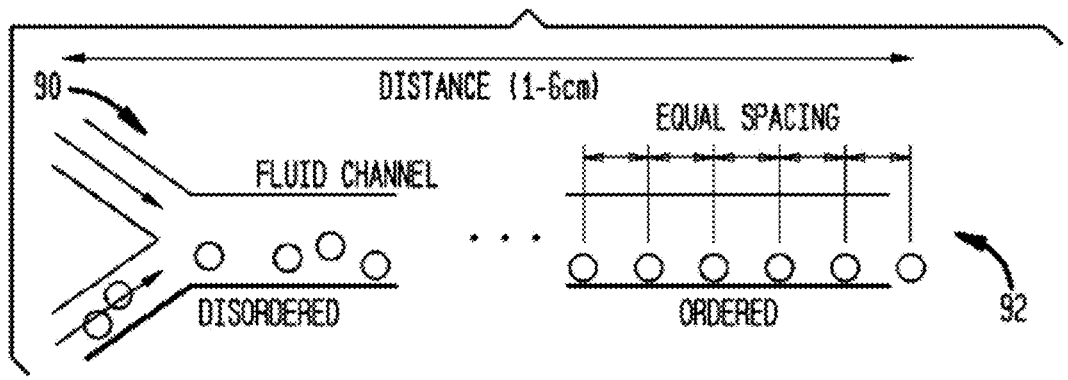

The ordering of particles, such as cells, in fluid passing through the channel 90 provides a tighter distribution in particle lateral position in the flow as well as improved particle-particle interactions leading to long regular chains 92 of particles with uniform spacing in the direction of flow, as shown in FIGS. 2B and 2C. Precision ordering of cells and particles of 5-15 µm in size can be demonstrated for a variety of particle/cell densities (<5%) at continuous flow, most clearly illustrated in FIG. 2B. Further, particles ordered in positions across the channel 90 also interact to create a uniform fluid buffer between them.

In one exemplary system having a 2:1 rectangular cross-sectional geometry, particles all travel with a speed of 13.2-13.8 cm/s (mean fluid velocity being 11.9 cm/s) and exhibit a center-center spacing of 42-45 µm between adjacent particles when they are focused to the same side of the channel 90, but are separated by only 23-25 µm in the direction of flow when the alternating pattern is present. These two patterns can also be found in combination, the particular ratio of one to the other depending most on the local concentration of particles; if the concentration is low, the particle-particle spacing present within the linear array is allowed, as shown in FIG. 2C. As the local concentration increases, however, particles are found more frequently in the interstitial sites on the other side of the channel 90, as illustrated in FIG. 2B. Equilibrium particle spacing at the end of a 6 cm channel is generally linearly dependent on the particle diameter and channel diameter.

Figure 2D:
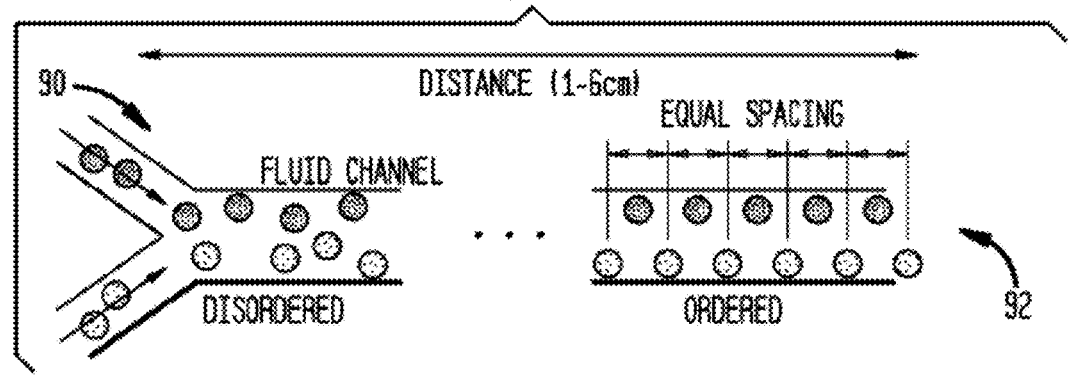

In another example shown in FIG. 2D, the conditions described with respect to FIGS. 2A-C are applied to particles of two different predetermined particle types. The particles 92 of a first type (illustrated as open circles) can be introduced into the channel through a first input branch (the lower branch), while a second particle type (illustrated as closed, shaded circles) can be introduced into the channel through a second separate channel branch, the upper input branch as shown in FIG. 2D. As shown, the two types of particles move from separate input branches into a single channel and are ordered and focused into two streams corresponding to two equilibrium positions on opposite sides of the channel. Where the first and second particles are differing cell types, particles having differing chemistries, or some combination thereof, having the particles focused and ordered such that the particles generally alternate between particles of the first type and particles of the second type as they travel down the channel allows for greater opportunities to observe and manipulate interactions between particles of the first and second types.

While the illustrated geometry for achieving the effects described with respect to FIG. 2 has an aspect ratio of 1 to 1, similar fluid particle self-effects may be observed with other aspect ratios. In addition to ratios of about 1 to 2, a reduction in symmetry can be observed in rectangular channels having dimensional ratios of approximately 15 to 50, 3 to 5, and 4 to 5. Accordingly, the fluid particle self-ordering effects can be seen for a dimensional aspect ratio of approximately 0.3 (15/50) to a dimensional aspect ratio of approximately 0.8 (4/5), and that the effects can be seen regardless of whether the longer dimension is the width or the height.

Figure 3:
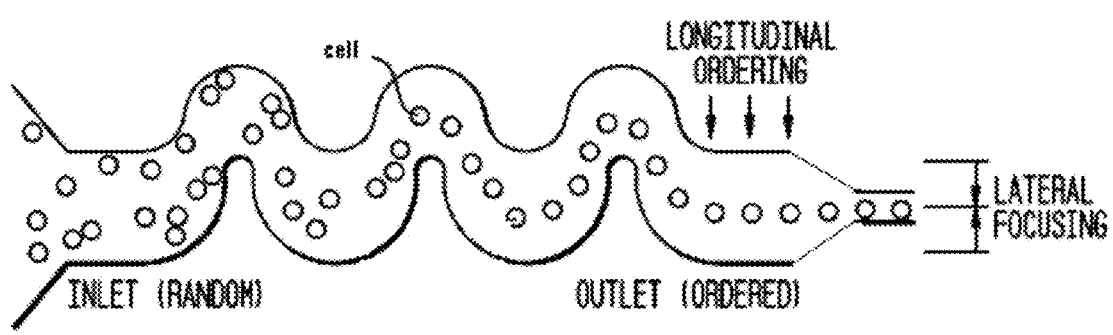
FIG. 3 is a schematic diagram showing the separation, ordering, and focusing of particles in a fluid passing through a symmetrically curved serpentine microfluidic channel.

Particles in a sample can also be ordered by passing the fluid sample through one or more symmetrically curved portions of a microfluidic channel. In general, as Rc increases between 0.5 and 5, focusing into two streams of particles in the fluid can occur. As Rc increases, mixed streams are again observed, in agreement with an increased contribution from Dean drag. FIG. 3 shows the separation, ordering, and focusing of particles in a fluid passing through a sserpentineal symmetrically curved microfluidic channel. An aspect ratio of a serpentine channel can be substantially 1 to 1 and/or can vary along a length thereof (e.g., the aspect ratio of a sserpentineal channel can vary over the length of the channel between 1 to 1 and 2 to 1). Particles are randomly distributed in the fluid at the inlet of the channel. As Rc increases between 0.5 and 5, focusing into two streams of particles can occur. As Rc increases, mixed streams are again observed, in agreement with an increased contribution from Dean drag.

The microchannel can also have one or more asymmetric curves, leading to a further reduction in the symmetry of particle focusing around the asymmetric curve region of the channel. In an asymmetrically shaped channel, the net force generally acts in one direction, biasing a single stable position of the initial distribution, and creating a single focused stream of particles. A time-averaged unidirectional centrifugal and/or drag force favors focusing down to a single stream between Re=1-15 Focusing becomes more complex as De increases. Particles are focused to one position of minimum potential with the addition of centrifugal forces or drag forces in the negative x-direction. Complete focusing can also occur for much smaller Rp of about 0.15 and for shorter traveled distances (about 3 mm) than in the case of straight rectangular channels.

Various methods can be used for identifying ordered and focused particles within a channel. Labels or tags for identifying or manipulating particles to be focused within the channels can be introduced into the sample before, during, and/or after introduction of the sample into the system. Labeling or tagging of particles is well known in the art for use, for example, in fluorescence-activated cell sorting (FACS) and magnetic-activated cell sorting (MACS), and any of the various methods of labeling can be used. Exemplary labeling methods and techniques are discussed in detail in U.S. Pat. No. 6,540,896 entitled, "Microfabricated Cell Sorter for Chemical and Biological Materials" filed May 21, 1999; U.S. Pat. No. 5,968,820 entitled, "Method for Magnetically Separating Cells into Fractionated Flow Streams" filed Feb. 26, 1997; and U.S. Pat. No. 6,767,706 entitled, "Integrated Active Flux Microfluidic Devices and Methods" filed Jun. 5, 2001; all of which are incorporated by reference in their entireties.

Various techniques exist for moving the sample through a microfluidic channel. For example, a microfluidic system can include a pumping mechanism for introducing and moving the fluid sample into and through one or more microfluidic channels. The pumping mechanism can also regulate and control a flow rate within the channels as needed. A specific pumping mechanism can be provided in a positive pumping configuration, in a negative pumping configuration, or in some combination of both. In one embodiment, a sample can be introduced into the inlet and can be pulled into the system under negative pressure or vacuum using the negative pumping configuration. A negative pumping configuration can allow for processing of a complete volume of sample, without leaving any sample within the channels. Exemplary negative pumping mechanisms can include, but are not limited to, syringe pumps, peristaltic pumps, aspirators, and/or vacuum pumps. In other embodiments, a positive pumping configuration can also be employed. A sample can be introduced into the inlet and can be injected or pushed into the system under positive pressure. Exemplary positive pumping mechanisms can include, but are not limited to, syringe pumps, peristaltic pumps, pneumatic pumps, displacement pumps, and/or a column of fluid. Oscillations caused by some pumping mechanisms, such as a peristaltic pump, can optionally be damped to allow for proper focusing within the channels.

Flow rates within the channels can be regulated and controlled. For instance, any number and variety of microfluidic valves can also be included in the system to block or unblock the pressurized flow of particles through the channels. The microvalve can include one or more mobile diaphragms or flexible membranes formed in a layer above a channel branch, inlet, or outlet such that upon actuation, the membrane is expanded up to decrease resistance within a channel branch, inlet, or outlet, or expanded down into the channel to increase resistance within the same. Further details and discussion of such microfluidic diaphragms are disclosed in PCT Publication No. PCT/US2006/039441 entitled, "Devices and Methods for Cell Manipulation" filed Oct. 5, 2007 and incorporated herein by reference in its entirety. Optionally, one or more microfluidic, size-based separation modules or filters can be included to prevent clogging within the channels by preventing certain particle sizes or particle types from entering the channels and/or to facilitate collection of particles for downstream processing.

The fluid stream of ordered particles can pass through an outlet of a microfluidic channel through a nozzle and into a medium suitable to induce droplet formation from the fluid stream. Droplet formation of the fluid can be induced by injecting the fluid into a second immiscible liquid, as described by Utada et al, Phys. Rev. Lett. 99, 094502 (2007), incorporated herein by reference in its entirety. The mechanism of droplet formation of the fluid is related to the presence of the surrounding viscous liquid. A liquid forced through an orifice will ultimately break into droplets at slow flows, whereas at faster flows the liquid forms a thin stream that breaks into droplets away from the orifice; these are the dripping and jetting regimes.

The transition between dripping and jetting in a two-phase coflowing stream. The behavior is characterized by a state diagram that depends on both the capillary number of the outer fluid, $C_{out}$, and the Weber number of the inner fluid, $W_{in}$; these parameters describe, respectively, the magnitude of the viscous shear forces from the outer liquid and the inertial forces from the inner liquid compared to surface tension forces. A transition from the drop-dripping to jetting behavior is dependent on the capillary number of the outer pinching flow $$(C_{out}=\eta_{out}u_{out}/\gamma),$$

and the Weber number for the inner flow, $$(W_{in}=\rho_{in}d_{tip}u_{in}^2/\gamma)$$

where $\rho$ is the density of the fluid, $\eta$ is the viscosity, $\gamma$ is the surface tension between the two phases, $d_{tip}$ is the diameter of the forming drop, and u is the fluid velocity. Both dimensionless numbers should be below O(1) to be certain of stable dripping behavior. Using these parameters, the droplet diameter of the fluid can be calculated based on the composition of the fluid and the immiscible liquid into which the fluid introduced after passing through a nozzle. Drop formation is affected by parameters including the average velocities of both liquids, their viscosities and densities, surface tension, and the surface chemistry and device geometry, as described by Utada et al, Phys. Rev. Lett. 99, 094502 (2007).

Figure 5:
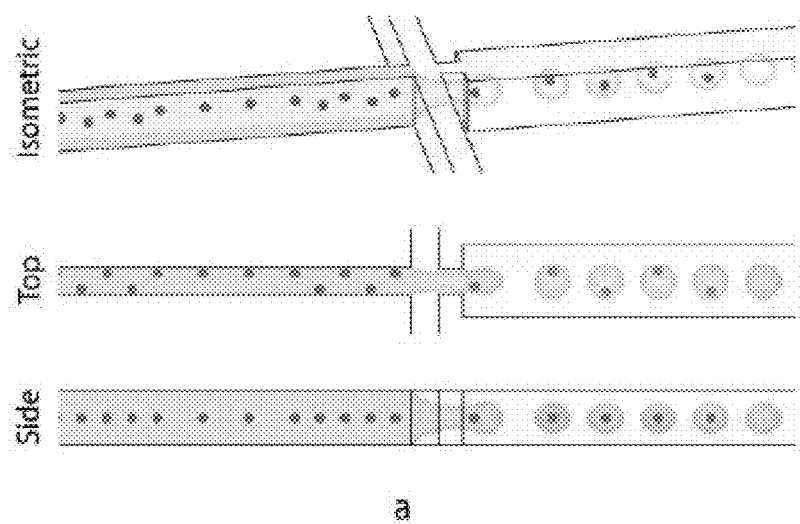
FIGS. 5A to 5C are a series of schematic representations of a straight microfluidic channel in an isometric view (5A), a top view (5B), and a side view (5C) that show the formation of droplets containing, on average, a single particle from a fluid stream of ordered particles within the microfluidic channel.
Figure 6:
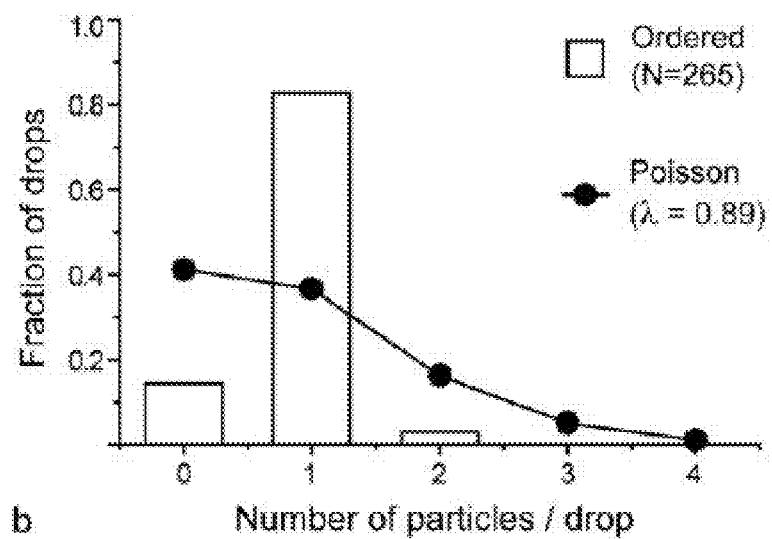
FIG. 6 is a graph of data showing the fraction of droplets generated with an indicated number of particles per droplet.
Figure 7A:
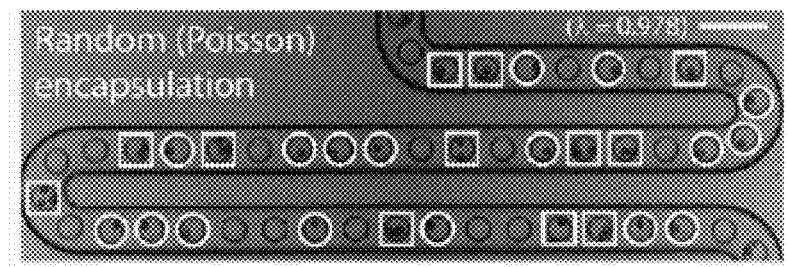
FIGS. 7A and 7B are optical micrographs of random (FIG. 7A) and ordered (FIG. 7B) encapsulation of particles in a fluid.
Figure 7B:
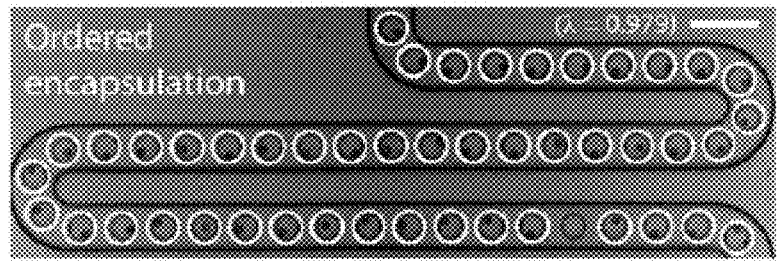

Within a straight microfluidic channel shown in FIG. 2A, hydrodynamic interactions can cause particles to self-organize along one side of the microchannel or into a diagonal/alternating pattern. The uniform spacing in the direction of flow (see side view) leads to the formation of single particle droplets when the two lateral flows of oil pull droplets from the aqueous stream (see isometric view) with the same (or higher) frequency that particles reach a microdrop generator (FIG. 5). As the results for 0.89 beads per drop on average in FIG. 6 indicate, ordered encapsulation of beads (FIGS. 7B, 8B) generates more single-particle droplets (circles) and fewer empty (not marked) or multiple-particle droplets (boxes) than would have been possible from FIG. 7A stochastic (Poisson) loading. FIG. 7A shows stochastic encapsulation of beads from a disordered (random) stream of beads, in contrast to the results for ordered encapsulation, FIG. 7B (46 out of 47 droplets contain a single bead) resulting from an ordered stream of particles in the fluid prior to droplet formation. Scale bars correspond to 100 micrometers.

Figure 8A:
FIGS. 8A and 8B are optical micrographs showing encapsulated droplet formation using beads (FIG. 8A) or cells (FIG. 8B).
Figure 8B:

Favorable conditions generated two main classes of organized behavior in the focusing channel preceding the drop generator (FIG. 5, top view): either (1) particles were focused into the same streamline along one side of the channel, or (2) particles were arranged into an array that alternated from one side of the channel to the other (FIG. 8A for beads and FIG. 8B for cells).

Figure 10A:
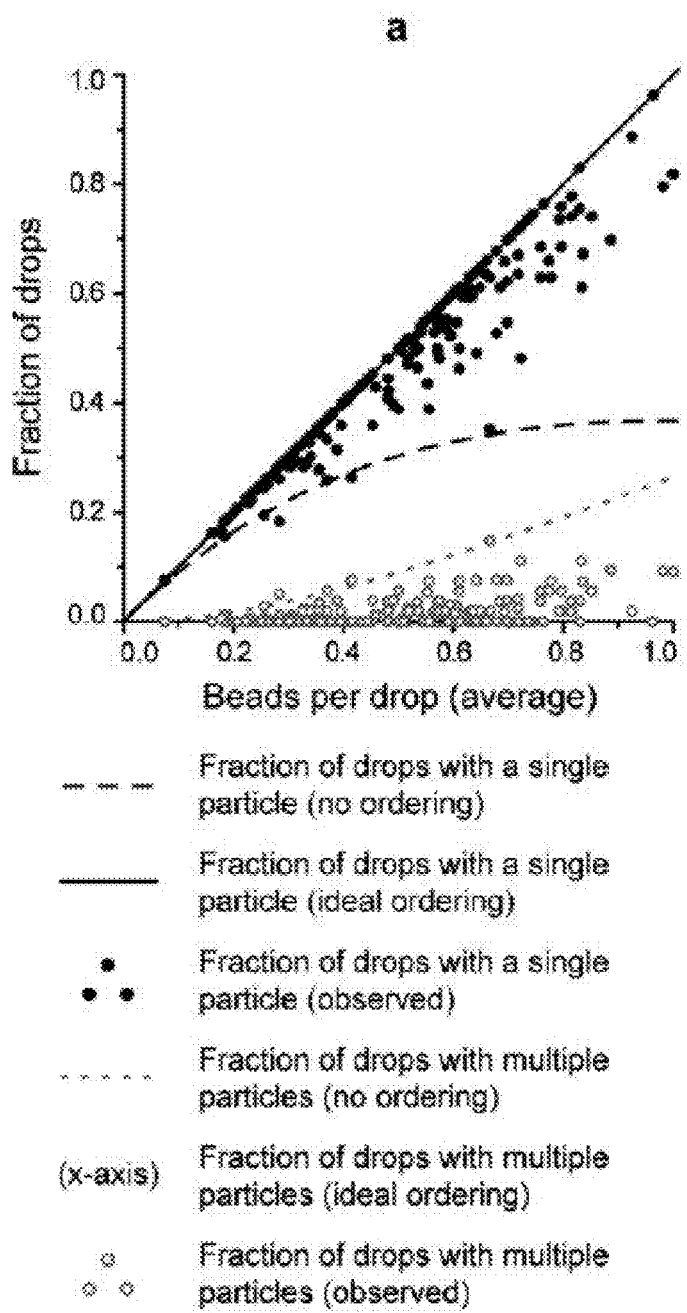
FIGS. 10A and 10B are graphs of data showing the fraction of droplets that contain a single particle and of droplets that contain more than one particle as a function of the average number of particles per droplet for (FIG. 10A) beads and (FIG. 10B) cells.
Figure 10B:
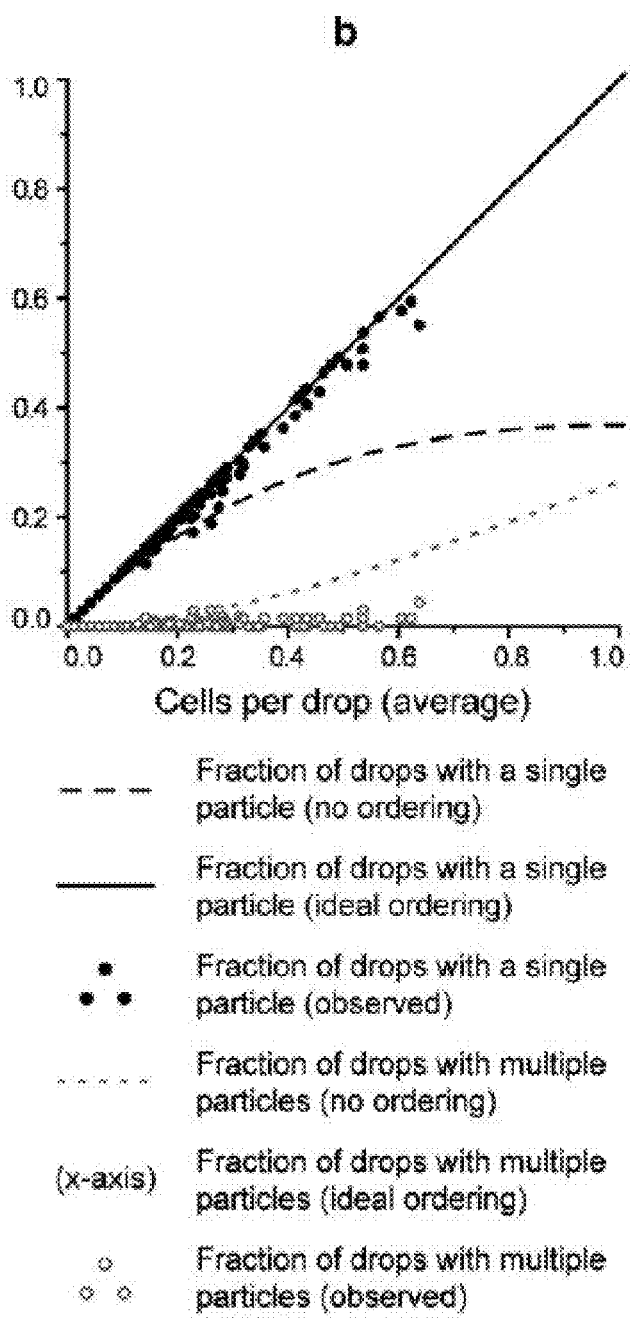

FIG. 10A and FIG. 10B are graphs showing the fraction of droplets as a function of particles (beads in FIG. 10A, cells in FIG. 10B). Each graph shows the resulting fractions of droplets that contain a single-particle (singles) and of droplets that contain multiple-particles (multiples) for concentrations between zero and one particles per drop. Nearly perfect single-particle loading (maximum fraction of singles is $\lambda$) is achieved in all cases and the results are far superior to those expected from Poisson statistics, especially for high concentrations. By fitting the dependences of singles and multiples to linear functions of $\lambda$, the ratio of singles to multiples can be calculated to be 30.9 for beads and 56.5 for cells.

From high-speed video recording, it is evident that most multiples resulted from particle aggregates that presumably formed when the initial batches of suspension were concentrated. Therefore, the rate of multiples should be proportional to $\lambda$, consistent with FIG. 10A-10B, which are graphs of data showing the fraction of droplets that contain a single-particle (singles) and of droplets that contain more than one particle (multiples) vs. average number of particles per drop ($\lambda$) for (FIG. 10A) beads and (FIG. 10B) cells. Data points (experiment) are plotted alongside curves expected for perfect (ordered) and random (Poisson) encapsulation. Fractions of singles fit a linear trend versus concentration, where they occurred with a frequency of $0.937\lambda$ for beads and $0.966\lambda$ for cells ($1\lambda$ is ideal). Multiples should not occur for perfect ordering but resulted sporadically from pre-existing particle aggregates ($0.0303\lambda$ and $0.0171\lambda$ for beads and cells, respectively). Each presented data point represents an analysis of 50-250 droplets in one of many wide-field frames of video, chosen at regular intervals from high-speed videos up to 5½ min long, totaling $8.42 \times 10^3$ beads in $18.9 \times 10^3$ droplets and $4.46 \times 10^3$ cells in $21.6 \times 10^3$ droplets. Moreover, perfect ordering appears limited only by these preexisting particle aggregates.

The two patterns of self-organized behavior noted above shared three distinctive characteristics: (1) each particle was separated from its nearest neighbor by a uniform spacing in the direction of flow, (2) particles were always found near the side walls of the channel, and (3) particles moved only in the direction of flow as a group. To ensure single-particle droplets, the flow of oil can be adjusted to generate droplets with a frequency not less than the frequency with which cells in the more closely-spaced alternating pattern of order arrived at the microdrop generator.

For example, to ensure that less than 2% of the occupied droplets are multiples, so that any misleading cross-talk between cells in the same drop is infrequent, Poisson statistics requires that cell suspension be diluted to $\lambda=0.040$, so that only 3.84% of all droplets contain a single-cell. However, the methods presented herein can provide over 20 times higher rates of single-cell droplets for the same ratio of singles to multiples.

The methods and devices disclosed herein can be used to encapsulate a variety of biological materials, particularly cells, in fluid droplets. The ability to rapidly analyze and extract information from whole blood, for example, and its component cells is of great importance for medical diagnostics and applications in basic science. Blood cells themselves contain an abundance of information relevant to disease, infection, malignancy, or allergy diagnosis. The methods and systems presented herein relate to inertial microfluidic technology as a solution for high throughput and precise microscale control of cell and particle motion. Methods and systems disclosed herein can be used for applications in blood cell subtype or rare cell enumeration, sorting, and analysis. Identification and analysis of rare cells, in particular, requires large sample sizes and high-throughput. The ability to sort, order, enumerate, and analyze particles continuously, differentially, and at high rates in a simple channel will be broadly applicable in a range of applications in continuous bio-particle separation, high-throughput cytometry, and large scale filtration systems.

The droplets can be formed using a nozzle in fluid communication with the outlet of a microfluidic channel formed in a microfluidic chip device. A microfabricated chip can be provided and can have any number and configurations of any of the channels described above formed therein. A plurality of the channels formed in the microfabricated chip that can be configured for receiving a sample introduced through the inlet and filter.

An analysis region can be provided in proximity to an output channels of the channels to monitor, sort, count, image, or otherwise analyze the focused streams of particles (e.g., cells). The output channels can be provided to receive and/or collect one or more focused streams of particles per channel after the streams travel through the analytical region of the chip. One or more output channels can also be provided for separating particles of a predetermined type away from a main stream of particles via a microfluidic valve. A controller, which can include any number of hardware, software, and analytical elements can be included to assist in pre-sample processing, pumping, flow rate regulation, valve operation, and any analysis to be performed on focused particles. After focusing, particles can be collected from the output channels into a reservoir or outlet for initial or additional analysis elsewhere, or for disposal.

A variety of techniques can be employed to fabricate the chip having channels formed therein for the separation, ordering, and focusing of particles. In one particular embodiment, the chip can be formed of PMMA. The features, including channels, can be transferred onto an electroformed mold using standard photolithography followed by electroplating. The mold can be used to hot emboss the features into the PMMA at a temperature near its glass transition temperature (105° C.) under pressure (5 to 20 tons). The mold can then be cooled to enable removal of the PMMA chip. A second piece used to seal the chip, composed of a similar or dissimilar material, can be bonded onto the first piece using vacuum-assisted thermal bonding. The vacuum prevents formation of air gaps in the bonding regions. As will be appreciated by those skilled in the art, the chip can be formed of any material or combination of materials as needed for specific pressure requirements within the channels, as well as specific channel geometries and size requirements.

EXAMPLES

The invention is further described in the following examples, which do not limit the scope of the invention described in the claims. Methods of making, analyzing, and characterizing some aspects of the polymer electrolytes are described below.

Unless otherwise indicated, the materials described herein were used to perform the examples below. Fluorescent polystyrene microparticles (density ~1.05 g/mL, 9.9 µm diameter, product #G1000) were purchased from Duke Scientific (Fremont, Calif.). Particles were mixed to desired weight fractions by dilution in Phosphate buffered saline (PBS) and stabilized by addition of 0.1% w/v Tween 20 (Sigma-Aldrich, St. Louis, Mo.). Cells (HL60 human promyelocytic leukemia cells, #CCL-240; ATCC, Manassas, Va.) were cultured in RPMI 1640 medium with 10% FBS and resuspended in PBS prior to use. A live-dead assay based on calcein AM and ethidium homodimer-2 (Invitrogen, Carlsbad, Calif.) was used to determine cell viability/membrane integrity according to established protocols.

For beads, FC-40 (3M, St. Paul, Minn.) were used with oil-phase surfactant courtesy of RainDance Technologies (Lexington, Mass.), who also provided the fluorinated oil and PFPE-PEG block copolymer surfactant mixture (1.8% w/w in oil) used in the cell experiments. A concentration of 0.1% w/w Zonyl FSN-100 (DuPont, Wilmington, Del.) was added to the aqueous phase for cell experiments to reduce biological interactions with the oil-water interface.

Microfluidic devices were fabricated using soft lithography techniques. SU-8 50 (MicroChem, Newton, Mass.) was spun at 2400 rpm for 30 seconds to create a 52 µm thick layer on a 10 cm silicon wafer. Thickness was measured using a Dektak profilometer. The pattern was photolithographically defined in this layer using a mylar mask printed at 50,000 dpi. After development, PDMS (Sylgard 184; Dow Corning, Midland, Mich.) was poured onto the SU-8 master at a 10:1 ratio of base to crosslinker, degassed in a vacuum chamber, and cured at 65° C. overnight. The devices were then cut from the mold; ports were subsequently punched with a sharpened flat tip needle and devices were bonded to glass slides using oxygen plasma. After plasma treatment and placement onto the glass substrate the devices were kept at 70° C. on a hotplate for 15 minutes to increase bonding. To ensure hydrophobic surfaces throughout the microchannels, and thus allow the oil to preferentially wet the channel walls, the contents of a 1 mL syringe was manually forced, filled with air and a small amount of Aquapel (PPG Industries, Pittsburgh, Pa.) inside the needle, through the channel network until no residue was visible. Channel width was measured optically during operational conditions.

Example 1

Formation of an Ordered Stream of Cells

Figure 4A:
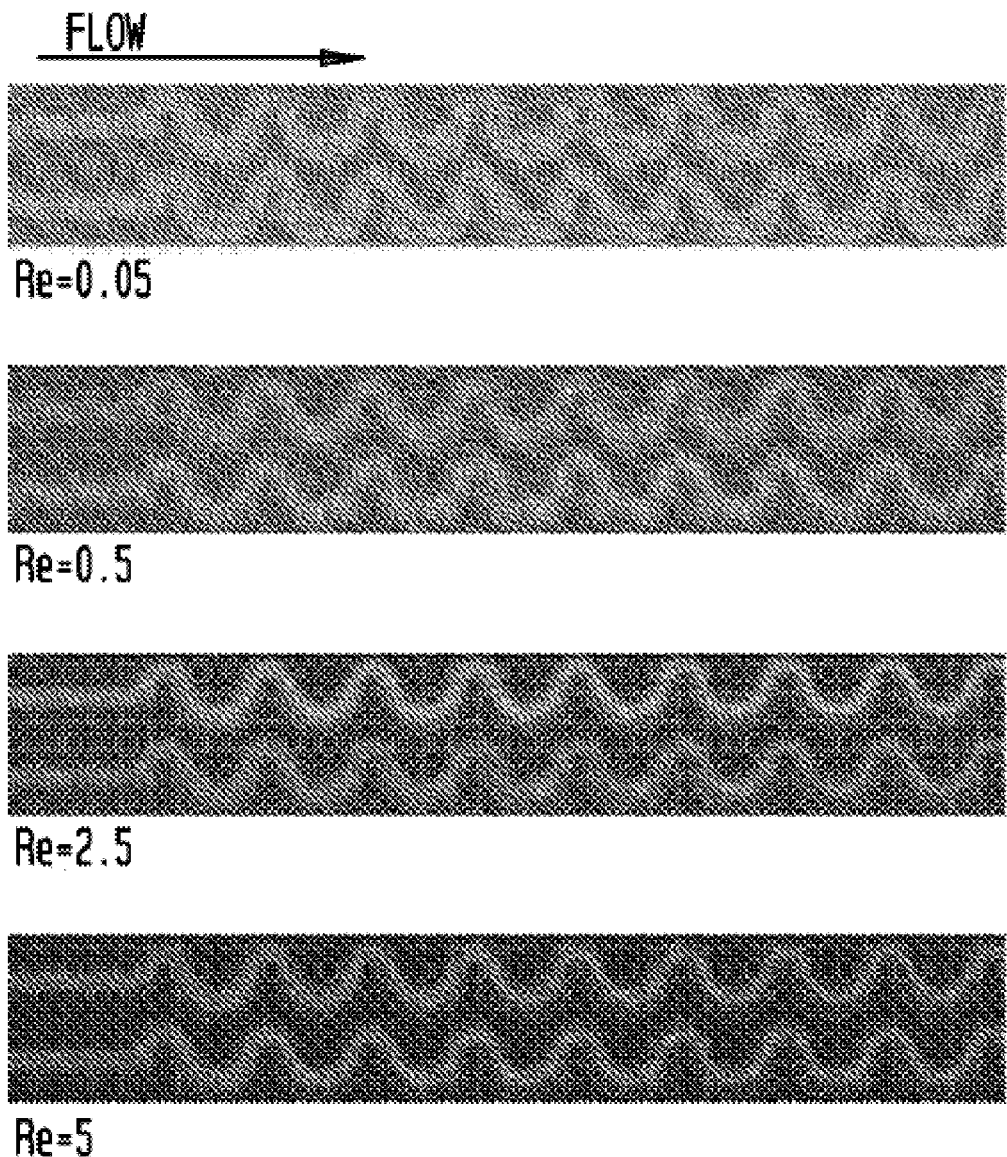
FIG. 4A shows a series of time-averaged images showing the focusing of cultured cells in a serpentine microfluidic channel at different Reynolds numbers based on the mean channel velocity ($R_e$) values from 0.05 to 5.0.

FIG. 4A illustrates focusing of blood cells in the same manner as rigid particles. Five percent whole blood diluted in PBS is run through rectangular channels of 50 µm width. At the outlet, 3 cm downstream, streak images of cells are observed in phase contrast. These appear as dark streams in the gray channel. The channel edges are also dark. As in the case with rigid particles 3 streaks are observed which correspond to four focus points on the rectangular channel faces.

Figure 4B:
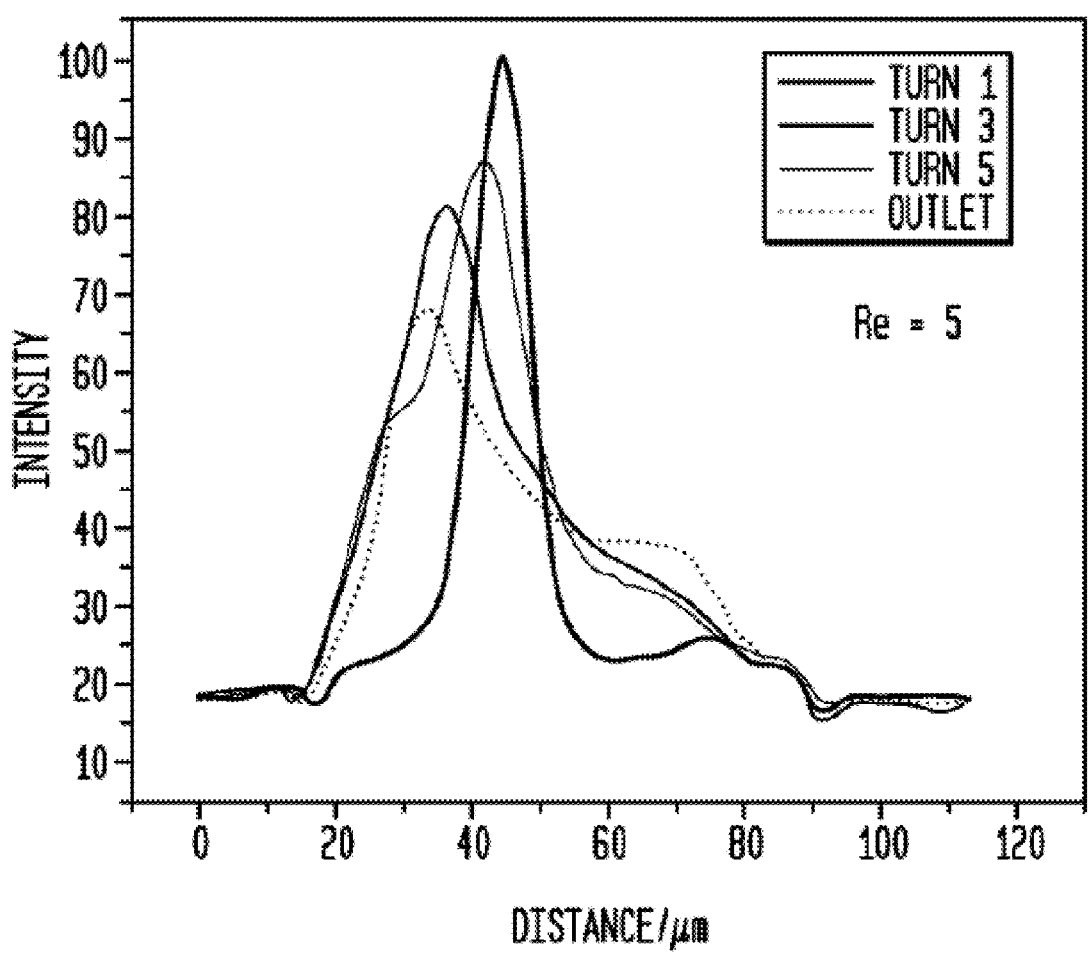
FIG. 4B is a graph showing the intensity cross sections at various turns and at the outlet of the microfluidic channel shown in FIG. 4A.

FIGS. 4A and 4B illustrate focusing of cultured cell lines. As with particles, deformable cells are focused to single streams. FIG. 4A shows streak images of cells focusing for various Re numbers are shown. The inlet of each focusing area is shown on the left. Focusing to a single lane starts to occur for $Re~2$ after 3 cm of travel. In FIG. 4B, intensity cross sections at various turns and at the outlet are shown. Note that at the outlet the width of the focused stream is comparable to the diameter of a single cell (~15 µm).

Cell viability can be maintained during inertial focusing. Because cells travel at high velocities (~0.5 m/s), it is important to evaluate cell viability and damage during this process. It should be noted that cells traveling at steady state with the fluid experience only small normal and shear stresses over their surfaces, while significant forces are briefly felt in the inlet and outlet regions where cells must be accelerated by the fluid. In the systems described herein, the channel width at the inlet can optionally be gradually tapered to minimize this effect. High cell viability is found by vital stain after passing through an exemplary system. The scatter plot width and position for blood before processing appeared essentially unchanged after passing through the system. Cell debris and blebbing would produce a broader distribution of scatter.

No significant alterations in cell viability occur after they are passed through the inertial focusing systems described herein at high speeds. Even at average velocities of 0.5 m/s there was no discernable damage to cells (99.0% vs. 99.8% initial viability as measured by using a fluorescent live/dead assay). High cell viability and throughput are important for applications such as flow cytometry.

Example 2

Encapsulation of Cells in Droplets

To demonstrate controlled single-cell microdrop generation, a flow-focusing geometry was used to emulsify concentrated suspensions of HL60 cells or 9.9 lm-diameter polystyrene beads immediately after they had traversed a 27 lm-wide×52 lm-tall×6 cm-long rectangular microchannel (See, e.g., S L Anna, *Applied Phys Lett*, 82, 364-366 (2003), incorporated herein by reference in its entirety).

Bead or cell suspensions and oil were separately introduced into two syringes and connected by either PEEK tubing (#1569; Upchurch Scientific, Oak Harbor, Wash.) or Tygon tubing (TGY-010; Small Parts) to the two inlets of the PDMS portion of the device. Outlets of PEEK tubing were also connected to the outlet ports of the device and routed into a waste container or collection tube.

Flow was driven at constant volume rate by a syringe pump (PHD 2000; Harvard Apparatus, Holliston, Mass.). A glass syringe (1 mL; SGE, Austin, Tex.) with an inserted magnetic stir bar was utilized to maintain well suspended solutions of particles prior to their injection, through a mechanism based on that reported recently where a steel ball bearing is moved magnetically within the syringe to induce mixing (R. Cooper and L. P. Lee, "Chips & Tips: Preventing suspension settling during injection," Lab on a Chip, 21 Aug. 2007). A plastic syringe (1 mL; BD, Franklin Lakes, N.J.) was used to drive oil with a flow rate of 50-60 μL/min for bead experiments and 85 μL/min for cell experiments. The aqueous flow was set to 10 μL/min for beads and 13 μL/min for cells. If precautions were not taken, clogging can occur as the entire suspension of particles funnels through one tiny orifice, the nozzle. A simple solution can be used for the incorporation of a microfluidic filter upstream of the focusing channel, at the site of the aqueous inlet. A series of narrow channels were included, slightly smaller in width than the narrowest point in the device, and they are arranged in a parallel fashion. Therefore, anything that enters the device that could clog the narrow nozzle region will be caught in the filter that immediately precedes the long focusing channel, thus preventing the device from clogging catastrophically. A 0.2 μm PTFE syringe filter (09-720-7; Fisher Scientific, Pittsburgh, Pa.) was used for the oil inlet.

PDMS devices were mounted onto the stage of an inverted microscope (Nikon TE2000-U). High-speed camera imaging was conducted using white light in Köhler illumination with the focal plane. All neutral density filters were removed and the highest power on the lamp allowed imaging with 2 μs exposures using a Phantom v4.2 camera (Vision Research, Wayne, N.J.). Frame intervals from 62.5 μs-100 ms were used.

Random arrangements of particles enter the inlet of the system and after traversing the ordering channel arrive at the droplet generator portion of the microfluidic system well ordered. The oil flow rate was tuned to match the frequency of drop generation with that of the ordering. The channel is 27 μm wide and particles are 10 μm in diameter.

For the experimental conditions employed, the center-to-center spacing between adjacent particles focused on the same side of the channel was 48.2±4.0 micrometers for beads and 33.5±3.7 micrometers for cells, corresponding to velocities of 13.7±0.1 cm/s and 20.6±0.7 cm/s, respectively. In comparison, the longitudinal spacing between particles that self-organized into the alternating pattern was reduced to 24.4±1.0 micrometers for beads and 19.0±2.0 micrometers for cells, corresponding to velocities of 13.70±0.04 cm/s and 21.1±0.3 cm/s, respectively.

The current system was operated at some of the fastest possible drop generation rates (~15 kHz). The system operated at this rate because the ordering phenomenon functions more robustly at higher channel velocities. The system is limited from going above this rate much further without changes in channel geometry due to a transition from the drop-dripping to jetting behavior. In the current system, further increases in drop generation rates could be achieved by tuning these parameters (e.g. by reducing surfactant concentrations to increase surface tension). Decreasing the viscosity of the outer flow could also yield dripping behavior at drop generation rates exceeding 15 kHz.

Figure 9A:
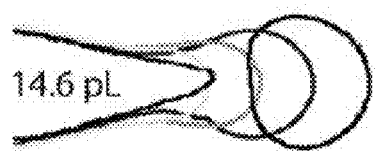
FIG. 9A shows the droplet formation process over time.
Figure 9B:
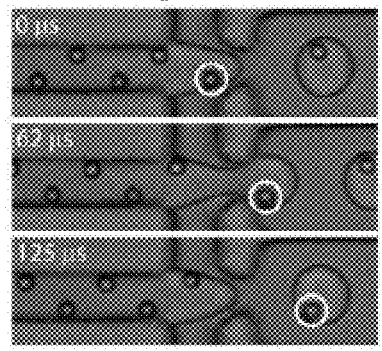
FIG. 9B is a series of three optical micrographs showing droplet formation using beads.

To ensure single-particle droplets, the flow of oil was adjusted to generate droplets with a frequency not less than the frequency with which cells in the more closely-spaced alternating pattern of order arrived at the microdrop generator. More precisely, the flow of oil was set to 50-60 microliters/min during bead experiments and 85 microliters/min during cell experiments, causing 21.7 pL droplets to form at 7.7 kHz for beads (see FIG. 9B) and 14.6 pL droplets to form at 14.9 kHz for cells (see FIG. 9A).

Figure 11:
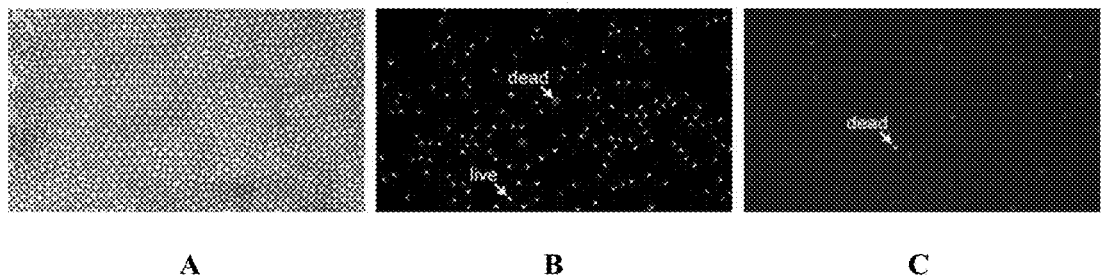
FIGS. 11A-11C are images of encapsulated cells were collected and flowed into a wide microfluidic chamber in a largely uniform emulsion shown in bright field (FIG. 11A), green fluorescence (FIG. 11B), and red fluorescence (FIG. 11C).

To confirm that the high aqueous flow rate required to induce self-ordering (aqueous flow rate was 10 microliter/min for beads and 13 microliter/min for cells) did not adversely affect the cells, their survival rates were tested after encapsulation and found that 92.9% of cells retained membrane integrity, as compared with 96.2% for controls (see FIG. 11A-C). Encapsulated cells were collected and flowed into a wide microfluidic chamber. Images of cells in the largely uniform emulsion are shown in bright field (a), green fluorescence (b), and red fluorescence (c). Exposure time was 500 ms for green fluorescence and 10 sec for red fluorescence. Cells were stained with a live/dead stain prior to encapsulation in the system. Cells that lost membrane integrity during the cell preparation process prior to entering the chip appear bright red (c), while cells with membranes disrupted during the single-cell encapsulation process leak green viability dye throughout the drop in which they were encapsulated (b). Live cells have higher intensity green signals (b) that did not spread throughout the drop in question. Scale bars: 100 μm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of encapsulating individual particles in a sample within individual liquid droplets, the method comprising flowing particles suspended within a sample through a microchannel, wherein the microchannel has an inlet and an outlet and a minimum cross-sectional dimension D, wherein a largest particle in a plurality of particles to be encapsulated has a maximum cross-sectional dimension that is at least about 0.1 D;

controlling a flow rate of the sample within the microchannel to have a channel Reynolds number (Rc) of about 1 to about 250 to form a substantially evenly-spaced, longitudinally ordered stream of particles in the sample within the microchannel, wherein the longitudinal ordering causes individual particles in the sample to exit the microchannel one at a time with a substantially uniform particle to particle spacing through the outlet and into a nozzle that is in fluid communication with the outlet; and controlling a flow rate of a fluid medium that is immiscible with the sample through two or more lateral channels connected to the nozzle at a velocity effective to generate individual liquid droplets of sample dispersed within the fluid medium, wherein the liquid droplets exit the nozzle and wherein the flow rates of the sample and fluid medium are controlled to produce a set of droplets in which a fraction of single-particle droplets is higher than the corresponding fraction of single-particle droplets predicted by Poisson statistics.

2. The method of claim 1, wherein the flow rate of the fluid sample and the flow rate of the fluid medium are controlled such that at least 80% of the set of droplets contain only one particle and fewer than 20% of the set of droplets contain zero particles.

3. The method of claim 1, wherein the flow rate of the sample and the flow rate of the fluid medium are controlled such that at least 90% of the set of droplets contain only one particle and fewer than 10% of the set of droplets contain zero particles.

4. The method of claim 1, wherein the plurality of particles to be encapsulated are of substantially the same size and wherein the largest particle in the plurality of particles to be encapsulated has a maximum cross-sectional dimension that is about 0.1 D to about 0.4 D.

5. The method of claim 1, wherein the flow rate of the sample within the first microchannel is controlled to form first and second substantially evenly-spaced, longitudinally ordered streams of particles in the fluid medium within the first microchannel, wherein the first and second ordered streams of particles are formed on opposite sides of the first microchannel, and wherein the particles in the first and second ordered streams move in an alternating pattern as they travel along the first microchannel.

6. The method of claim 5, wherein the longitudinal order of the first and second substantially evenly-spaced, longitudinally ordered streams of particles is shifted by half of a particle-particle spacing.

7. The method of claim 1, wherein the first microchannel is straight.

8. The method of claim 1, wherein the first microchannel is curved and has a Dean number of up to about 30.

9. The method of claim 8, wherein the first microchannel is symmetrically curved and wherein a channel Reynolds number (Rc) of between about 0.5 and 5.0 causes focusing of particles into two longitudinally ordered streams of particles.

10. The method of claim 8, wherein the first microchannel is asymmetrically curved and a channel Reynolds number (Rc) of between about 1.0 and 15.0 causes focusing of particles into a single longitudinally ordered stream of particles.

11. The method of claim 8, wherein the first microchannel is asymmetrically curved and a mean channel velocity (Re) is set to about 2.5 to 5.0, wherein Re equals 2/3 of the channel Reynolds number (Rc).

12. The method of claim 8, wherein the Dean number for the curved first microchannel ranges from about 1 to about 20, and wherein a ratio of particle size to hydraulic diameter of the first microchannel is less than about 0.5.

13. The method of claim 1, wherein the particle Reynolds number (Rp) is at least about 0.15.

14. The method of claim 1, wherein the particles are cells.

15. The method of claim 1, wherein the sample is an aqueous sample and wherein the particles are cells.

16. The method of claim 1, wherein the fluid medium is an oil.

17. The method of claim 1, wherein the flow rate of the fluid medium is maintained at a velocity effective to generate droplets with a frequency not less than the frequency with which particles leave the first microchannel.

18. The method of claim 17, wherein the droplets are formed at a rate of no more than about 15 kHz.

19. The method of claim 1, wherein the sample is passed through the first microchannel at a flow rate of at least about 10 microliters/minute.

20. The method of claim 1, wherein the first microchannel has a rectangular cross section, and a cross-sectional aspect ratio of about 1.5 to 8.0.

* * * * *

UNITED STATES PATENT AND TRADEMARK OFFICE
CERTIFICATE OF CORRECTION

| | | |
|---|---|---|
| PATENT NO. | : 9,677,064 B2 | Page 1 of 1 |
| APPLICATION NO. | : 14/754420 | |
| DATED | : June 13, 2017 | |
| INVENTOR(S) | : Jon F. Edd et al. | |

It is certified that error appears in the above-identified patent and that said Letters Patent is hereby corrected as shown below:

On the Title Page

Column 1, under Inventors:
Delete "Memhet" and Insert -- Mehmet --

In the Specification

Column 1, Line 11 (approx.):
After "application" Delete "is incorporated herein by reference in its entirety." and
Insert -- and U.S. Patent are incorporated herein by reference in their entireties. --

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*